United States Patent [19]

Lesher et al.

[11] 4,331,672

[45] May 25, 1982

[54] 5-(PYRIDINYL)PYRIDINE-2-HYDRAZINES, THEIR PREPARATION AND THEIR CARDIOTONIC USE

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 231,312

[22] Filed: Feb. 4, 1981

Related U.S. Application Data

[63] Continuation-in-part of Ser. No. 135,100, Mar. 28, 1980.

[51] Int. Cl.$^3$ .................... C07D 401/04; A61K 31/44
[52] U.S. Cl. ..................................... 424/263; 546/257; 546/258
[58] Field of Search ................ 546/257, 258; 424/263

[56] References Cited

FOREIGN PATENT DOCUMENTS 1322318  7/1973  United Kingdom .

Primary Examiner—John M. Ford
Attorney, Agent, or Firm—Robert K. Bair; B. Woodrow Wyatt

[57] ABSTRACT

2-[$R_1$NHN(R)]-3-Q'-5-Py-6-Q-pyridines or pharmaceutically-acceptable acid-addition salts thereof are useful as cardiotonic agents, where Q is hydrogen or lower-alkyl, PY is 4- or 3-pyridinyl or 4- or 3-pyridinyl having one or two lower-alkyl substituents, Q' is hydrogen or halo, R is hydrogen, lower-alkyl or lower-hydroxyalkyl, and $R_1$ is hydrogen or when R is other than hydrogen $R_1$ is the same as R. These compounds are prepared by reacting a 2-halo-3-Q'-5-PY-6-Q-pyridine with $R_1$NHNHR where 2-halo is bromo or chloro. Also shown are: the use of said 2-[$R_1$NN(R)]-3-Q'-5-PY-6-Q-pyridines as cardiotonic agents; and, the intermediates, 2,3-dihalo-5-PY-6-Q-pyridines, and their preparation from 3-nitro-5-PY-6-Q-2(1H)-pyridinones.

14 Claims, No Drawings

5-(PYRIDINYL)PYRIDINE-2-HYDRAZINES, THEIR PREPARATION AND THEIR CARDIOTONIC USE

CROSS-REFERENCE TO RELATED APPLICATIONS

This application is a continuation-in-part of copending application Ser. No. 135,100, filed Mar. 28, 1980, which discloses 5-(pyridinyl)pyridine-2-hydrazines claimed herein as intermediates for preparing 5-(pyridinyl)pyridin-2-amines.

The 5-(pyridinyl)-6-(lower-alkyl)-2(1H)-pyridinones which are used herein as intermediates are disclosed and claimed as cardiotonics in copending application Ser. No. 204,726, filed Nov. 6, 1980, and also are disclosed as intermediates in said copending parent application Ser. No. 135,100 and in copending applications Ser. Nos. 198,461, filed Oct. 20, 1980, as well as 135,105 and 135,211, both filed Mar. 28, 1980.

The 2-halo-5-PY-6-Q-pyridines and 2-halo-3-nitro-5-PY-6-Q-pyridines which also are used herein as intermediates are disclosed and claimed in said copending parent application Ser. No. 135,100.

BACKGROUND OF THE INVENTION (a) Field of the Invention

This invention relates substituted pyridine-2-hydrazines, their preparation, their salts, intermediates therefor and their use as cardiotonics.

(b) Description of the Prior Art

Lesher and Gruett British Pat. No. 1,322,318, published July 4, 1973, shows as intermediates for preparing antibacterially-active 1-alkyl-1,4-dihydro-4-oxo-7-PY-1,8-naphthyridine-3-carboxylic acids and esters (where PY is 4- or 3-pyridinyl or 4- or 3-pyridinyl having one or two lower-alkyl substituents) the following illustrative reaction sequence (Examples 1C through 1G and 2C through 2G): the preparation of 1,2-dihydro-2-oxo-6-(4- or 3-pyridinyl)-nicotinonitrile, its hydrolysis and decarboxylation to produce 6-(4- or 3-pyridinyl)-2(1H)-pyridinone, its chlorination with phosphorus oxychloride to produce 2-chloro-6-(4- or 3-pyridinyl)pyridine, its reaction with hydrazine to produce 2-hydrazino-6-(4- or 3-pyridinyl)pyridine and its catalytic hydrogenation using Raney nickel to produce 2-amino-6-(4- or 3-pyridinyl)pyridine, which is useful as an intermediate to produce said antibacterially-active 1,8-naphthyridines.

SUMMARY OF THE INVENTION

In a composition of matter aspect, the invention resides in 2-[$R_1$NHN(R)]-3-Q'-5-PY-6-Q-pyridine (I) or pharmaceutically-acceptable acid-addition salt thereof, which is useful as a cardiotonic agent and/or as an intermediate, where $R_1$, R, Q', PY and Q are defined hereinbelow.

A composition aspect of the invention resides in a cardiac composition for increasing cardiac contractility, said composition comprising a pharmaceutically-acceptable carrier and, as the active component thereof, a cardiotonically-effective quantity of 2-[$R_1$NHN(R)]-3-Q'-5-PY-6-Q-pyridine or pharmaceutically-acceptable acid-addition salt thereof.

In a method aspect, the invention resides in a method for increasing cardiac contractility in a patient requiring such treatment which comprises administering to said patient a medicament comprising a pharmaceutically-acceptable carrier and, as the active component thereof, a cardiotonically-effective amount of 2-[$R_1$NHN(R)]-3-Q'-5-PY-6-Q-pyridine or pharmaceutically-acceptable acid-addition salt thereof.

In a process aspect, the invention resides in the process which comprises reacting 2-halo-3-Q'-5-PY-6-Q-pyridine with $R_1$NHNHR to produce 2-[$R_1$NHN(R)]-3-Q'-5-PY-6-Q-pyridine.

In another process aspect, the invention resides in the process which comprises reacting 3-nitro-5-PY-6-Q-2(1H)-pyridinone with a halogenating agent to produce 2,3-dihalo-5-PY-6-Q-pyridine.

In another composition of matter aspect, the invention resides in 2,3-dihalo-5-PY-6-Q-pyridine(II) or pharmaceutically-acceptable acid-addition salt thereof, useful as an intermediate in said process aspect of the invention.

DETAILED DESCRIPTION INCLUSIVE OF PREFERRED EMBODIMENTS

In a composition of matter aspect the invention resides in a 2-[$R_1$NHN(R)]-3-Q'-5-PY-6-Q-pyridine having the formula I

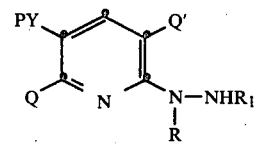

or pharmaceutically-acceptable acid-addition salt thereof, where Q is hydrogen or lower-alkyl, PY is 4- or 3-pyridinyl or 4- or 3-pyridinyl having one or two lower-alkyl substituents, Q' is hydrogen or halo, R is hydrogen, lower-alkyl or lower-hydroxyalkyl, and $R_1$ is hydrogen or when R is other than hydrogen $R_1$ is the same as R. The compounds of formula I are useful as cardiotonic agents, as determined by standard pharmacological evaluation procedures. The compounds of formula I where R and $R_1$ are each hydrogen are useful as intermediates for preparing the corresponding 3-Q'-5-PY-6-Q-pyridin-2-amines of said parent copending application Ser. No. 135,100. Preferred embodiments of the compounds of formula I are those where Q is hydrogen, methyl or ethyl, PY is 4-pyridinyl or 3-pyridinyl, Q' is chloro or hydrogen, R is hydrogen, methyl, ethyl or 2-hydroxyethyl, and $R_1$ is either hydrogen or the same as R, that is, methyl, ethyl or 2-hydroxyethyl respectively.

The composition aspect of the invention resides in a cardiotonic composition for increasing cardiac contractility, said composition comprising a pharmaceutically-acceptable carrier and, as the active component thereof, a cardiotonically-effective amount of a 2-[$R_1$NHN(R)]-3-Q'-5-PY-6-Q-pyridine having formula I or pharmaceutically-acceptable acid-addition salt thereof, where $R_1$, R, Q', PY and Q have the meanings given for formula I. Preferred embodiments are those containing as active component the compounds of formula I where Q is hydrogen, methyl or ethyl, PY is 4-pyridinyl or 3-pyridinyl, Q' is chloro or hydrogen, R is hydrogen, methyl, ethyl or 2-hydroxyethyl, and $R_1$ is either hydrogen or the same as R.

A method aspect of the invention resides in the method for increasing cardiac contractility in a patient requiring such treatment which comprises administering orally or parenterally in a solid or liquid dosage form to such patient a medicament comprising a pharmaceutically-acceptable carrier and, as active component thereof, a cardiotonically-effective amount of a 2-[R₁NHN(R)]-3-Q'-5-PY-6-Q-pyridine having formula I or pharmaceutically-acceptable acid-addition salt thereof, where R₁, R, Q', PY and Q have the meanings given for formula I. Preferred embodiments are those using as active component the compounds of formula I where Q is hydrogen, methyl or ethyl, PY is 4-pyridinyl or 3-pyridinyl, Q' is chloro or hydrogen, R is hydrogen, methyl, ethyl or 2-hydroxyethyl and R₁ is either hydrogen or the same as R.

In a process aspect the invention resides in the process which comprises reacting 2-halo-3-Q'-5-PY-6-Q-pyridine with R₁NHNHR to produce 2-[R₁NHN(R)]-3-Q'-5-PY-6-Q-pyridine, where 2-halo is bromo or chloro, and Q', PY, Q, R₁ and R have the meanings given above for formula I. Preferred aspects are those where 2-halo is chloro and the products produced by the process are the above-noted preferred embodiments of formula I.

In another process aspect, the invention resides in the process which comprises reacting 3-nitro-5-PY-6-Q-2(1H)-pyridinone with a halogenating agent, preferably phenylphosphonic dichloride, phosphorus oxychloride or phosphorus oxybromide, to produce 2,3-dihalo-5-PY-6-Q-pyridine (II) where halo is chloro or bromo, and PY and Q have the meanings given below for formula II. Preferred embodiments are those which produce the compounds (II) where PY is 4-pyridiny or 3-pyridinyl, and Q is hydrogen, methyl or ethyl.

In another composition of matter aspect, the invention resides in 2,3-dihalo-5-PY-6-Q-pyridine having the formula II

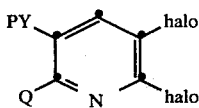

or pharmaceutically-acceptable acid-addition salts thereof, where halo is chloro or bromo, PY and Q have the meanings given above for formula I. These compounds (II) are useful as intermediates in the process shown hereinabove. Preferred embodiments are those where halo is chloro, PY is 4-pyridinyl or 3-pyridinyl and Q is hydrogen, methyl or ethyl.

The term "lower-alkyl" as used herein, e.g., as one of the meanings of Q, R or R₁, or as a substituent for PY, in formula I or II, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-hydroxyalkyl," as used herein, e.g., as one of the meanings for R or R₁ in formula I, means hydroxyalkyl radicals having from two to six carbon atoms and having its hydroxy group and its free valence bond (or connecting linkage) on different carbon atoms, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxypentyl, 6-hydroxyhexyl, and the like.

Illustrative of PY in formula I or II where PY is 4- or 3-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds of formulas I and II are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound (I or II) are prepared either by dissolving the free base in aqueous or aqueous-alcohol solution or other suitable solvents containing the appropriate acid and isolating the salt by evaporating the solution, or by reacting the free base and acid in organic solvent, in which case the salt separates directly or can be obtained by concentration of the solution.

Although pharmaceutically-acceptable salts of said basic compound (I or II) are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structures of the compounds of formulas I and II were assigned on the basis of evidence provided by infrared, nuclear magnetic resonance and mass spectra, and by the correspondence of calculated and found values for elemental analyses.

The manner of making and using the instant invention will now be generally described so as to enable a person skilled in the art of pharmaceutical chemistry to make and use the same, as follows.

The preparation of the 1,2-dihydro-2-oxo-5-PY-6-R-nicotinonitriles, which are used as intermediates to prepare 5-PY-6-(lower-alkyl)-2(1H)-pyridinones, are described in the next three paragraphs. These intermediate nicotinonitriles are disclosed and claimed as cardiotonics in copending application Ser. No. 198,461, filed Oct. 20, 1980.

The preparation of 1-PY-2-(dimethylamino)ethenyl lower-alkyl ketone by reacting PY-methyl lower-alkyl ketone with dimethylformamide di-(lower-alkyl)acetal is carried out by mixing the reactants in the presence or absence of a suitable solvent. The reaction is conveniently run at room temperature, i.e., about 20°–25° C., or by warming the reactants up to about 100° C., preferably in an aprotic solvent, conveniently hexamethylphosphoramide because of the method used to prepare the PY-methyl lower-alkyl ketone, as noted below in Example A-1. Other suitable solvents include tetrahydrofuran, dimethylformamide, acetonitrile, ether, benzene, dioxane, and the like. Also, the reaction can be run without solvent, preferably using an excess of dimethylformamide di-(lower-alkyl)acetal. This procedure is further illustrated hereinbelow in Examples A-1 through A-13.

The intermediate PY-methyl lower-alkyl ketones are generally known compounds which are prepared by known methods [e.g., as given in Rec. trav. chim 72, 522 (1953); U.S. Pat. No. 3,133,077 (5-12-64); Bull. Soc. Chim. 1968, 4132; Chem. Abstrs. 79, 8539h (1973); Chem. Abstrs. 81, 120,401a (1974); J. Org. Chem. 39, 3834 (1974); Chem. Abstrs. 87, 6594q (1977); J. Org. Chem. 43, 2286 (1978)].

The reaction of 1-PY-2-(dimethylamino)ethenyl lower-alkyl ketone with α-cyanoacetamide to produce 1,2-dihydro-2-oxo-5-PY-6-(lower-alkyl)nicotinonitrile is carried out preferably by heating the reactants in a suitable solvent in the presence of a basic condensing agent. The reaction is conveniently run using an alkali lower-alkoxide, preferably sodium methoxide or ethoxide, in dimethylformamide. In practicing the invention, the reaction was carried out in refluxing dimethylformamide using sodium methoxide. Alternatively, methanol and sodium methoxide or ethanol and sodium ethoxide can be used as solvent and basic condensing agent, respectively; however, a longer heating period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like. This procedure is further illustrated hereinbelow in Examples B-1 through B-12.

The conversion of 1,2-dihydro-2-oxo-5-PY-6-(lower-alkyl)nicotinonitrile to 5-PY-6-(lower-alkyl)-2(1H)-pyridinone is carried out by heating said nicotinonitrile with an aqueous mineral acid, preferably 50% sulfuric acid, first to form the corresponding nicotinic acid and then continue heating for a longer period whereupon the nicotinic acid is decarboxylated to produce 5-PY-6-(lower-alkyl)-2(1H)-pyridinone. This procedure is further illustrated hereinbelow in Examples C-1 through C-11.

The corresponding 1,2-dihydro-2-oxo-5-PY-6-Q-nicotinonitriles and 5-PY-6-Q-2(1H)-pyridinones, as well as 3-nitro-5-PY-6-Q-2(1H)-pyridinones, where Q is hydrogen are shown in U.S. Pat. No. 4,072,746. As illustrated hereinbelow in Examples D-1 through D-12, the corresponding 3-nitro-5-PY-6-(lower-alkyl)-2(1H)-pyridinones can be prepared following the procedure described in Example C-1 of U.S. Pat. No. 4,072,746 by reacting the corresponding 1,2-dihydro-2-oxo-5-PY-6-(lower-alkyl)nicotinonitrile with concentrated nitric acid whereby the nitrile is first converted to the corresponding nicotinic acid, which on heating is decarboxylated followed by formation of said 3-nitro compound.

The reaction of a 5-PY-6-Q-2(1H)-pyridinone with an inorganic halogenating agent to produce a 2-halo-5-PY-6-Q-pyridine is preferably carried out by refluxing the 2(1H)-pyridinone with excess phosphorus oxychloride containing a catalytic amount of dimethylformamide to obtain the 2-chloro compound. Other suitable inorganic halogenating agents include $PCl_3$, $POBr_3$, $PBr_3$, $PCl_5$, phenylphosphonic dichloride, and the like. This reaction is further illustrated below in Examples E-1 through E-18.

The reaction of 3-nitro-5-PY-6-Q-2(1H)-pyridinone with phenylphosphonic dichloride to produce 2,3-dichloro-5-PY-6-Q-pyridine is carried out by heating the reactants at about 175° C. to 250° C., preferably about 200° C. to 225° C. in the absence of any solvent; optionally the reaction can be run in the presence of a suitable inert solvent, e.g., nitrobenzene, 1,2,3-trichlorobenzene, 1,2,4-trichlorobenzene and 1,3,5-trichlorobenzene. Alternatively, the preparation of 2,3-dichloro-5-PY-6-Q-pyridine can be carried out by heating 3-nitro-5-PY-6-Q-2(1H)-pyridinone with phosphorus oxychloride in an autoclave or optionally 2,3-dibromo-5-PY-6-Q-pyridine can be prepared by using phosphorus oxybromide in place of phosphorus oxychloride. This reaction is further illustrated hereinbelow in Examples F-1 through F-17.

Alternatively, the 2,3-dihalo-5-PY-6-Q-pyridines of formula II can be prepared reacting a 3-halo-5-PY-6-Q-2(1H)-pyridine with an inorganic halogenating agent to produce a 2,3-dihalo-5-PY-6-Q-pyridine in the same manner shown above for converting a 5-PY-6-Q-2(1H)-pyridine to a 2-halo-5-PY-6-Q-pyridine. This reaction is illustrated below in Examples F-18 through F-30. The intermediate 3-halo-5-PY-6-Q-2(1H)-pyridinones where Q is hydrogen are known [U.S. Pat. No. 4,072,746] and where Q is lower-alkyl are disclosed in said copending Application Serial No. 198,461. The intermediate 3-halo-5-PY-6-(lower-alkyl)-2(1H)-pyridinones are shown in said copending Application Ser. No. 198,461. These compounds are prepared by reacting the corresponding 5-(PY)-6-(lower-alkyl)-2(1H)-pyridinone with halogen; this preparation is carried out by mixing the reactants in an appropriate solvent inert under the reaction conditions, a preferred solvent being acetic acid. The reaction is conveniently run at room temperature or by heating the reactants at temperatures up to about 100° C. Preferred halogens are bromine an chlorine. Any inert solvent can be used, e.g., dimethylformamide, chloroform, acetic acid, and the like. This procedure is illustrated further hereinbelow in Examples H-1 through H-22.

The reaction of 2-halo-3-Q'-5-PY-6-Q-pyridine with $R_1NHNHR$ to produce 2-[$R_1NHN(R)$]-3-Q'-5-PY-6-Q-pyridine is carried out by mixing the reactants at about room temperature (20°–25° C.) to 150° C., preferably about 50° C. to 100° C., and preferably in the presence of a suitable inert solvent, e.g., isopropyl alcohol, ethanol, dioxane, ethylene glycol, and the like. This reaction is further illustrated hereinbelow in Examples G-1 through G-36.

The following examples will further illustrate the invention without, however, limiting it thereto.

A. 1-PY-2-(DIMETHYLAMINO)ETHENYL LOWER ALKYL KETONES

A-1.—1-(4-Pyridinyl)-2-(dimethylamino)ethenyl methyl ketone—A mixture containing 20 g. of (4-pyridinyl)-methyl methyl ketone [alternatively named 1-(4-pyridinyl)-2-propanone] and 30 ml. of hexamethylphosphoramide was diluted with 65 ml. of dimethylformamide dimethyl acetal and the resulting mixture was refluxed for 30 minutes. TLC analysis showed a single spot, thereby indicating completion of the reaction (in another run, the reaction appeared to be complete after 30 minutes at room temperature). The reaction mixture was evaporated under reduced pressure using a rotary evaporator and a pressure of about 15 mm., thereby resulting in a crystalline residue weighing 24 g. The residue was purified by continuous chromatographic extraction on alumina (about 150 g.) using chloroform (recycled by distillation onto the alumina) as eluant. After 1 and ½ hours, the extract was heated in vacuo to remove the chloroform, thereby leaving, as a light yellow crystalline material, 23.2 g. of 1-(4-pyridinyl)-2-(dimethylamino)ethenyl methyl ketone, alternatively named 4-dimethylamino-2-(4-pyridinyl)-3-buten-2-one.

The above preparation can be carried out using in place of hexamethylphosphoramide other solvents, e.g., dimethylformamide, acetonitrile or others noted above or in the absence of a solvent; however, hexamethylphosphoramide was conveniently used since (4-pyridinyl)methyl methyl ketone was conveniently prepared as a mixture together with hexamethylphosphoramide, as seen by the following preparation: To a stirred solution containing 70 ml. of freshly distilled diisopropylamine and 200 ml. of tetrahydrofuran at 0° C. under nitrogen was added dropwise over 20 minutes 210 ml. of 2.4 M n-butyllithium in n-hexane and the reaction mixture was stirred for about 35 minutes at about 0°–5° C. To the cold solution was added dropwise over a period of 10 minutes 90 ml. of dry hexamethylphosphoramide (no temperature change) and a resulting light yellow solution was stirred for 15 minutes. To the cold solution at 0° C. was added a solution of 50 ml. of 4-picoline in 150 ml. of dry tetrahydrofuran over a 15 minute period and stirring was continued for 30 minutes at 0° C. Next, a mixture containing 50 ml. of dry ethyl acetate and 150 ml. of tetrahydrofuran was added over a 15 minute period (temperature rose from 0° to about 6° C.) and the resulting mixture was stirred for 20 minutes at 0° C. The ice bath was then removed and stirring continued for another 90 minutes whereupon the temperature of the reaction mixture rose to about 25° C. The reaction mixture was then cooled in an ice bath and to it was added 60 ml. of acetic acid over a period of about 30 minutes. The tetrahydrofuran was distilled off using a rotary evaporator in vacuo. The remaining mixture was diluted with 400 ml. of water and the aqueous mixture was extracted successively with two 250 ml. portions of isopropyl acetate and three 80 ml. portions of chloroform. The solvents were distilled off under reduced pressure to yield about 137 g. of a mixture consisting primarily of the desired product and hexamethylphosphoramide. Another run using the same quantities was carried out as above except after the addition of 60 ml. of glacial acetic acid, the mixture was diluted with only 200 ml. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g., b.p. of 110°–112° C. at 4 mm.; II. 59 g. of pale yellow oil, b.p. 113°–115° C. at 3 mm.; and, III. 69 g. of pale yellow oil, b.p. 115°–118° C. at 2.5 mm. Examination of fraction III by NMR showed it to consist of a 2:3 mixture by weight of (4-pyridinyl)methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl mixture ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively the monolactate or monohydrochloride salt in aqueous solution.

A-2.—1-(4-Pyridinyl)-2-(dimethylamino)ethenyl ethyl ketone—A mixture containing 87.5 g. of (4-pyridinyl)methyl ethyl ketone [alternatively named 1-(4-pyridinyl)-2-butanone] and 160 ml. of hexamethylphosphoramide was diluted with 100 g. of dimethylformamide dimethyl acetal and the resulting mixture was stirred under nitrogen at room temperature for 45 minutes. The methanol formed by the reaction was distilled off in vacuo using a rotary evaporator and the remaining material was distilled under reduced pressure to yield two fractions, one boiling at 45°–80° C. at 0.5 mm. and the second at 90°–95° C. at 0.5 mm. After TLC analysis showed predominantly a single spot for each fraction, the two fractions were combined (135 g.) and taken up in 600 ml. of chloroform. The resulting solution was washed with two 300 ml. portions of water and the water was back extracted with three 100 ml. portions of chloroform. The combined chloroform solution was dried over anhydrous sodium sulfate and purified by continuous extraction chromatography on 300 ml. of alumina using chloroform (recycled by distillation onto the alumina) as the eluant. The chloroform was distilled off in vacuo to yield a red oil which crystallized on standing overnight in an ice bath. The crystalline material was dissolved in carbon tetrachloride, cyclohexane was added and the mixture cooled to yield 64 g. of the resulting yellow crystalline product, 1-(4-pyridinyl)-2-(dimethylamino)ethenyl ethyl ketone. Another 11 g. of crystalline product was obtained from the mother liquor by continuous extraction chromatography on alumina using chloroform (recycled by distillation onto the alumina) as the eluant.

The above intermediate (4-pyridinyl)methyl ethyl ketone was obtained in a mixture with hexamethylphosphoramide as follows: To a mixture containing 200 ml. of tetrahydrofuran and 70 ml. of diisopropylamine under nitrogen at 0°–5° C. was added 210 cc. of 2.4 N n-butyllithium in n-hexane and the resulting mixture was stirred for 30 minutes. Next was added over a 10 minute period 90 ml. of hexamethylphosphoramide followed by stirring of the mixture for 15 minutes. Then was added over a 15 minute period a solution of 48 ml. of 4-picoline in 150 ml. of tetrahydrofuran followed by stirring for 30 minutes at about 0° C. The ice/acetone bath cooling the reaction mixture was replaced with a dry ice/acetone bath and to the reaction mixture was added over a 20 minute period a mixture of 75 ml. of ethyl propionate in an equal volume of tetrahydrofuran. The reaction mixture was then allowed to warm up to room temperature over a period of about 90 minutes and then was warmed at about 35° C. for 30 minutes. The mixture was next cooled in an ice/acetone bath and to it was added 60 ml. of glacial acetic acid over 30 minutes. The resulting pale yellow suspension was diluted with 200 ml. of water. The mixture was extracted with three 150 ml. portions of ethyl acetate and the ethyl acetate extract was back washed with saline solution. The extract was heated in vacuo to remove the ethyl acetate and the residue was taken up again with ethyl acetate. The solution was washed with water and then heated in vacuo to remove the ethyl acetate followed by heating the residue in vacuo at 50° C. for about 30 minutes to yield 100 g. of pale yellow oil. The pale yellow oil was combined with corresponding samples obtained from two additional runs and then distilled in vacuo to yield a 256 g. fraction, b.p. 85°–105° C. at 0.5–1.0 mm. The NMR of this fraction showed it to be a mixture of (4-pyridinyl)methyl ethyl ketone and hexamethylphosphoramide in a respective molar ratio of 1:1.55, that is, 35% or 0.35×256=90 g. of said ketone.

A-3. 1-(4-Pyridinyl)-2-(dimethylamino)ethenyl n-propyl ketone—A mixture containing 80 g. of (4-pyridinyl)methyl n-propyl ketone [alternatively named 1-(4-pyridinyl)-2-pentanone] and 46 ml. of hexamethylphosphoramide was diluted with 250 ml. of acetonitrile. To the mixture was added 90 ml. of dimethylformamide dimethyl acetal and the resulting mixture was heated on a steam bath for ninety minutes and then distilled under vacuum at about 2 mm. to remove volatile materials, including methanol, acetonitrile and hexamethylphosphoramide. The remaining residue was diluted with ethyl acetate and washed with water. The combined water washings were extracted with five 150 ml. portions of ethyl acetate. The combined ethyl acetate solutions were washed with saline solution, dried over anhydrous sodium sulfate, filtered and evaporated to dryness. The residue crystallized while standing in a freezer. The crystalline product was slurried with cyclohexane, filtered and dried overnight at 30° C. to produce, as a yellow crystalline product, 97 g. of 1-(4-pyridinyl)-2-(dimethylamino)ethenyl n-propyl ketone, m.p. 48°–50° C.

The above intermediate (4-pyridinyl)methyl n-propyl ketone was obtained in a mixture with hexamethylphosphoramide as follows: To a stirred solution of 70 ml. of diisopropylamine in 200 ml. of tetrahydrofuran under nitrogen at about 0° C. (use of ice bath) was added 210 ml. of 2.4 N n-butyllithium over twenty minutes and the resulting mixture was stirred for 30 minutes at about 0° C. to the mixture was added with stirring over ten minutes 90 ml. of hexamethylphosphoramide and the resulting mixture was stirred for another ten minutes. Next 45 ml. of 4-picoline in 140 ml. of tetrahydrofuran was added dropwise over fifteen to twenty minutes. The resulting dark orange-brown solution was stirred at 0° C. for thirty minutes and then treated dropwise over an eighteen minute period a solution consisting of 68 ml. of ethyl butyrate in 68 ml. of tetrahydrofuran, the temperature rising from −8° C. to +8° to 10° C. The reaction mixture was removed from the ice bath and allowed to warm up to room temperature over seventy-five minutes. The reaction mixture was re-cooled and to it was added dropwise over fifteen minutes 60 ml. of glacial acetic acid. A pale yellow solid separated, resulting in a suspension. The suspension was diluted with water and extracted with two 200 ml. portions of ethyl acetate. The ethyl acetate extract was washed with three 100 ml. portions of saline solution, dried over anhydrous sodium sulfate and evaporated in vacuo to yield 107 g. of a mixture consisting primarily of (4-pyridinyl)methyl n-propyl ketone and hexamethylphosphoramide. The mixture obtained in this run was combined with corresponding mixtures obtained in two other runs and the combined mixtures were distilled under vacuum to produce, as the major fraction, b.p. 80°–90° C. at 0.2 mm., a mixture consisting of 80 g. of (4-pyridinyl)-methyl n-propyl ketone and 46 g. of hexamethylphosphoramide.

Following the procedure described in Example A-2 but using a molar equivalent quantity of the appropriate PY-methyl lower-alkyl ketone in place of (4-pyridinyl)methyl ethyl ketone, it is contemplated that the corresponding 1-PY-2-(dimethylamino)ethenyl lower-alkyl ketones of Examples A-4 thru A-17 can be obtained.

A-4. 1-(3-Pyridinyl)-2-(dimethylamino)ethenyl methyl ketone using (3-pyridinyl)methyl methyl ketone.

A-5. 1-(4-Pyridinyl)-2-(dimethylamino)ethenyl isopropyl ketone using (4-pyridinyl)methyl isopropyl ketone.

A-6. 1-(4-Pyridinyl)-2-(dimethylamino)ethenyl n-butyl ketone using (4-pyridinyl)methyl n-butyl ketone.

A-7. 1-(4-Pyridinyl)-2-(dimethylamino)ethenyl isobutyl ketone using (4-pyridinyl)methyl isobutyl ketone.

A-8. 1-(4-Pyridinyl)-2-(dimethylamino)ethenyl tert.-butyl ketone using (4-pyridinyl)methyl tert.-butyl ketone.

A-9. 1-(4-Pyridinyl)-2-(dimethylamino)ethenyl n-pentyl ketone using (4-pyridinyl)methyl n-pentyl ketone.

A-10. 1-(2-Methyl-4-pyridinyl)-2-(dimethylamino)ethenyl ethyl ketone using (2-methyl-4-pyridinyl)methyl ethyl ketone.

A-11. 1-(3-Pyridinyl)-2-(dimethylamino)ethenyl ethyl ketone using (3-pyridinyl)methyl ethyl ketone.

A-12. 1-(4-Pyridinyl)-2-(dimethylamino)ethenyl n-hexyl ketone using (4-pyridinyl)methyl n-hexyl ketone.

A-13. 1-(2,6-Dimethyl-4-pyridinyl)-2-(dimethylamino)ethenyl methyl ketone using (2,6-dimethyl-4-pyridinyl)methyl methyl ketone.

B.

1,2-DIHYDRO-6-(LOWER-ALKYL)-2-OXO-5-PY-NICOTINONITRILES

B-1.—1,2-Dihydro-6-methyl-2-oxo-5-(4-pyridinyl)-nicotinonitrile, alternatively named 1,6-dihydro-2-methyl-6-oxo-[3,4'-bipyridine]-5-carbonitrile–To a mixture containing 23 g. of 1-(4-pyridinyl)-2-(dimethylamino)ethenyl methyl ketone and 11 g. of α-cyanoacetamide dissolved in 400 ml. of dimethylformamide was added with stirring 14 g. of sodium methoxide and the resulting mixture was heated in an oil bath under gentle reflux for one hour. TLC analysis showed no starting material in the reaction mixture which was then concentrated in vacuo on a rotary evaporator to a volume of about 80 ml. The concentrate was treated with about 160 ml. of acetonitrile and the resulting mixture was stirred on a rotary evaporator with warming until homogeneous and then cooled. The crystalline product was collected, rinsed successively with acetonitrile and ether, and dried overnight at 55° C. to yield 28 g. of tan crystalline product, namely, sodium salt of 1,2-dihydro-6-methyl-2-oxo-5-(4-pyridinyl)nicotinonitrile, the presence of cyano being confirmed by IR analysis. An 8 g. portion of said sodium salt was dissolved in 75 ml. of hot water, the aqueous solution treated with decolorizing charcoal filtered, the filtrate again treated with decolorizing charcoal and filtered, and the filtrate acidified with 6 N-hydrochloric acid by dropwise addition to a pH of 3. The acidic mixture was diluted with ethanol and cooled. The crystalline product was collected, dried, recrystallized from dimethylformamide-water and dried to produce 3.75 g. of 1,2-dihydro-6-methyl-2-oxo-5-(4-pyridinyl)nicotinonitrile, m.p. >300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in aabout 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinonitrile and the appropriate acid, e.g., lactic acid or hydrochloric acid, to prepare respectively the monolactate or monohydrochloride salt in aqueous solution.

B-2.—6-Ethyl-1,2-dihydro-2-oxo-5-PY-nicotinonitrile, alternatively named 2-ethyl-1,6-dihydro-6-oxo[3,4'-bipyridine]-5-carbonitrile, m.p. >300° C., 11.6 g., was prepared following the procedure described above in Example B-1 using 20 g. of 1-(4-pyridinyl)-2-(dimethylamino)ethenyl ethyl ketone, 8.4 g. of α-cyanoacetamide, 16.2 g. of sodium methoxide and 250 ml. of dimethylacetamide (as solvent in place of dimethylformamide).

B-3.—1,2-Dihydro-2-oxo-6-n-propyl-5-(4-pyridinyl)-nicotinonitrile, alternatively named 1,6-dihydro-6-oxo-2-n-propyl-[3,4'-bipyridine]-5-carbonitrile, m.p. 232°-234° C., 9.9 g., was prepared following the procedure described above in Example B-1 using 85 g. of 1-(4-pyridinyl)-2-(dimethylamino)ethenyl n-propyl ketone, 36.5 g. of α-cyanoacetamide, 50 g. of sodium methoxide and 800 ml. of dimethylacetamide.

Following the procedure described in Example B-2 but using a molar equivalent quantity of the appropriate 1-PY-2-(dimethylamino)ethenyl lower-alkyl ketone in place of 1-(4-pyridinyl)-2-(dimethylamino)ethenyl ethyl ketone and the appropriate α-cyanoacetamide, it is contemplated that the corresponding 1,2-dihydro-2-oxo-5-PY-6-R-nicotinonitriles of Examples B-4 thru B-12 can be obtained.

B-4. 1,2-Dihydro-6-methyl-2-oxo-5-(3-pyridinyl)-nicotinonitrile, using 1-(3-pyridinyl)-2-(dimethylamino)ethenyl methyl ketone and α-cyanoacetamide.

B-5. 1,2-Dihydro-6-isopropyl-2-oxo-5-(4-pyridinyl)-nicotinonitrile, using 1-(4-pyridinyl)-2-(dimethylamino)ethenyl isopropyl ketone and α-cyanoacetamide.

B-6. 6-n-Butyl-1,2-dihydro-2-oxo-5-(4-pyridinyl)-nicotinonitrile, using 1-(4-pyridinyl)-2-(dimethylamino)ethenyl n-butyl ketone and α-cyanoacetamide.

B-7. 1,2-Dihydro-6-isobutyl-2-oxo-5-(4-pyridinyl)-nicotinonitrile, using 1-(4-pyridinyl)-2-(dimethylamino)ethenyl isobutyl ketone and α-cyanoacetamide.

B-8. 1,2-Dihydro-2-oxo-5-(4-pyridinyl)-6-tert.-butyl-nicotinonitrile, using 1-(4-pyridinyl)-2-(dimethylamino)ethenyl tert.-butyl ketone and α-cyanoacetamide.

B-9. 1,2-Dihydro-2-oxo-6-n-pentyl-5-(4-pyridinyl)-nicotinonitrile, using 1-(4-pyridinyl)-2-(dimethylamino)ethenyl n-pentyl ketone and α-cyanoacetamide.

B-10. 6-Ethyl-1,2-dihydro-5-(2-methyl-4-pyridinyl)-2-oxonicotinonitrile, using 1-(2-methyl-4-pyridinyl)-2-(dimethylamino)ethenyl ethyl ketone and α-cyanoacetamide.

B-11. 6-Ethyl-1,2-dihydro-2-oxo-5-(3-pyridinyl)-nicotinonitrile, using 1-(3-pyridinyl)-2-(dimethylamino)ethenyl ethyl ketone and α-cyanoacetamide.

B-12. 1,2-Dihydro-5-(2,6-dimethyl-4-pyridinyl)-6-methyl-2-oxonicotinonitrile, using 1-(2,6-dimethyl-4-pyridinyl)-2-(dimethylamino)ethenyl methyl ketone and α-cyanoacetamide.

C.
6-(LOWER-ALKYL)-5-PY-2(1H)-PYRIDINONES

C-1. 6-Methyl-5-(4-pyridinyl)-2(1H)-pyridinone, alternatively named 2-methyl-[3,4'-bipyridin]-6(1H)-one—A mixture of 5.3 g. of 1,2-dihydro-6-methyl-2-oxo-5-(4-pyridinyl)nicotinonitrile and 30 ml. of 85% sulfuric acid was heated to about 195° C., gently refluxed for twenty-four hours, cooled and added to ice. The aqueous mixture was brought to a pH of 8 by addition of concentrated aqueous sodium hydroxide solution. The resulting precipitate (product plus Na$_2$SO$_4$) was treated with chloroform and the chloroform solution filtered. The filtrate was concentrated in vacuo to remove the chloroform and the resulting crystalline residue was recrystallized from methylene dichloride-ether and dried at 75° C. for four hours to produce 4.1 g. of 6-methyl-5-(4-pyridinyl)-2(1H)-pyridinone, m.p. 287°-288° C.

Acid-addition salts of 6-methyl 5-(4-pyridinyl)-2(1H)-pyridinone are conveniently prepared by adding to a mixture of 5 g. of 6-methyl-5-(4-pyridinyl)-2(1H)-pyridinone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 6-methyl-5-(4-pyridinyl)-2(1H)-pyridinone and the appropriate acid, e.g., lactic acid or hydrochloric acid, to prepare respectively the monolactate or monohydrochloride salt in aqueous solution.

C-2. 6-Ethyl-5-(4-pyridinyl)-2(1H)-pyridinone, alternatively named 2-ethyl-[3,4'-bipyridin]-6(1H)-one—A mixture containing 9 g. of 6-ethyl-1,2-dihydro-2-oxo-5-(4-pyridinyl)nicotinonitrile and 50 ml. of concentrated sulfuric acid was heated with stirring at 200° C. for twenty-four hours, cooled to about 40° C. and quenched in 200 ml. of ice water. After the aqueous solution had been basified with concentrated ammonium hydroxide, the separated solid was collected, recrystallized from isopropyl alcohol (70 ml.), and dried at 60° C. in vacuo to yield 3 g. of 6-ethyl-5-(4-pyridnyl)-2(1H)pyridinone, m.p. 226°-228° C. A second crop of 0.4 g., m.p.

225°-227° C., was obtained by concentrating the filtrate to about 20 ml.

C-3. 6-n-Propyl-5-(4-pyridinyl)-2(1H)-pyridinone, alternatively named 2-(n-propyl)-[3,4'-bipyridin]-6(1H)-one, m.p. 179°-180° C., 3.4 g., was obtained following the procedure described in Example C-2 but using 10 g. of 1,2-dihydro-6-n-propyl-2-oxo-5-(4-pyridinyl)nicotinonitrile, 42.5 ml. of 85% sulfuric acid, and recrystallization from methylene dichloride-ether.

Following the procedure described in Example C-2 but using in place of 6-ethyl-1,2-dihydro-2-oxo-5-(4-pyridinyl)nicotinonitrile a molar equivalent quantity of the corresponding 1,2-dihydro-2-oxo-5-PY-6-(lower-alkyl)nicotinonitrile, it is contemplated that there can be obtained the 5-PY-6-(lower-alkyl)-2(1H)-pyridinones of Examples C-4 through C-12.

C-4. 6-Methyl-5-(3-pyridinyl)-2(1H)-pyridinone.
C-5. 6-Isopropyl-5-(4-pyridinyl)-2(1H)-pyridinone.
C-6. 6-n-Butyl-5-(4-pyridinyl)-2(1H)-pyridinone.
C-7. 6-Isobutyl-5-(4-pyridinyl)-2(1H)-pyridinone.
C-8. 5-(4-Pyridinyl)-6-tert.-butyl-2(1H)-pyridinone.
C-9. 6-n-Pentyl-5-(4-pyridinyl)-2(1H)-pyridinone.
C-10. 6-Ethyl-5-(2-methyl-4-pyridinyl)-2(1H)-pyridinone.
C-11. 6-Ethyl-5-(3-pyridinyl)-2(1H)-pyridinone.
C-12. 6-Methyl-5-(2,6-dimethyl-4-pyridinyl)-2(1H)-pyridinone.

D. 6-(LOWER-ALKYL)-3-NITRO-5-PY-2(1H)-PYRIDINONES

Following the procedure described in Example C-1 of U.S. Pat. No. 4,072,746 but using in place of 1,2-dihydro-2-oxo-5-(4-pyridinyl)nicotinic acid a molar equivalent quantity of the corresponding 1,2-dihydro-2-oxo-5-PY-6-(lower-alkyl)-nicotinic acid, it is contemplated that there can be obtained the 3-nitro-5-PY-6-(lower-alkyl)-2(1H)-pyridinones of Examples D-1 through D-11.

D-1. 6-Methyl-3-nitro-5-(4-pyridinyl)-2(1H)-pyridinone.
D-2. 6-Ethyl-3-nitro-5-(4-pyridinyl)-2(1H)-pyridinone.
D-3. 6-Methyl-3-nitro-5-(3-pyridinyl)-2(1H)-pyridinone.
D-4. 3-Nitro-6-n-propyl-5-(4-pyridinyl)-2(1H)-pyridinone.
D-5. 3-Nitro-6-isopropyl-5-(4-pyridinyl)-2(1H)-pyridinone.
D-6. 6-n-Butyl-3-nitro-5-(4-pyridinyl)-2(1H)pyridinone.
D-7. 6-Isobutyl-3-nitro-5-(4-pyridinyl)-2(1H)pyridinone.
D-8. 3-Nitro-5-(4-pyridinyl)-6-tert.-butyl-2(1H)-pyridinone.
D-9. 3-Nitro-6-n-pentyl-5-(4-pyridinyl)-2(1H)-pyridinone.
D-10. 6-Ethyl-3-nitro-5-(2-methyl-4-pyridinyl)-2(1H)-pyridinone.
D-11. 6-Ethyl-3-nitro-5-(3-pyridinyl)-2(1H)-pyridinone.

E. 2-HALO-5-PY-6-Q-PYRIDINES

E-1. 2-Chloro-5-(4-pyridinyl(pyridine, alternatively named 6-chloro-[3,4'-bipyridine]—A mixture containing 105 g. of 5-(4-pyridinyl)-2(1H)-pyridinone and 1 liter of phosphorus oxychloride was heated on a steam bath for two hours and then allowed to stand at room temperature overnight. The excess phosphorus oxychloride was distilled off in vacuo and the remaining material poured into ice. The aqueous mixture was made weakly basic with ammonium hydroxide. The precipitate was collected, washed with water and dried in vacuo at 70° C. to yield 108 g. of 2-chloro-5-(4-pyridinyl)pyridine.

Following the above procedure but using in place of phosphorus oxychloride a molar equivalent quantity of phosphorus oxybromide or phosphorus tribromide, it is contemplated that the corresponding compound of Example E-2 can be obtained.

E-2. 2-Bromo-5-(4-pyridinyl)pyridine.

Following the procedure described in Example E-1 but using in place of 5-(4-pyridinyl)-2(1H)pyridinone a molar equivalent quantity of the corresponding 5-PY-6-Q-2(1H)-pyridinone, it is contemplated that the corresponding 2-chloro-5-PY-6-Q-pyridines of Examples E-3 through E-18 can be obtained.

E-3. 2-Chloro-5-(3-pyridinyl)pyridine.
E-4. 2-Chloro-5-(2-methyl-3-pyridinyl)pyridine.
E-5. 2-Chloro-5-(5-methyl-3-pyridinyl)pyridine.
E-6. 2-Chloro-5-(3-ethyl-4-pyridinyl)pyridine.
E-7. 2-Chloro-6-methyl-5-(4-pyridinyl)pyridine.
E-8. 2-Chloro-6-ethyl-5-(4-pyridinyl)pyridine.
E-9. 2-Chloro-6-methyl-5-(3-pyridinyl)pyridine.
E-10. 2-Chloro-6-n-propyl-5-(4-pyridinyl)pyridine.
E-11. 2-Chloro-6-isopropyl-5-(4-pyridinyl)pyridine.
E-12. 6-n-Butyl-2-chloro-5-(4-pyridinyl)pyridine.
E-13. 2-Chloro-6-isobutyl-5-(4-pyridinyl)pyridine.
E-14. 2-Chloro-5-(4-pyridinyl)-6-tert.-butylpyridine.
E-15. 2-Chloro-6-n-pentyl-5-(4-pyridinyl)pyridine.
E-16. 2-Chloro-6-ethyl-5-(2-methyl-4-pyridinyl)pyridine.
E-17. 2-Chloro-6-ethyl-5-(3-pyridinyl)pyridine.
E-18. 2-Chloro-6-methyl-5-(2,6-dimethyl-4-pyridinyl)pyridine.

F. 2,3-DIHALO-5-PY-6-Q-PYRIDINES

F-1. 2,3-Dihalo-5-(4-pyridinyl)pyridine—A mixture containing 31 g. of 3-nitro-5-(4-pyridinyl)-2(1H)-2-pyridinone, and 150 ml. of phenylphosphonic dichloride was heated on an oil bath at 210°-220° C. for two hours and then allowed to cool. The reaction mixture was poured into ice and water and the aqueous mixture was basified with ammonium hydroxide while stirring. The separated product was collected, washed with water and dried. It was then recrystallized from isopropyl alcohol and dried to yield 17 g. of 2,3-dichloro-5-(4-pyridinyl)pyridine, m.p. 274°-275° C. with decomposition.

Acid-addition salts of 2,3-dichloro-5-(4-pyridinyl)-pyridine are conveniently prepared by adding to a mixture of 5 g. of 2,3-dichloro-5-(4-pyridinyl)pyridine in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 2,3-dichloro-5-(4-pyridinyl)pyridine and the appropriate acid, e.g., lactic acid or hydrochloric acid, to prepare respectively the monolactate or monohydrochloride salt in aqueous solution.

Following the procedure described in Example F-1 but using in place of 3-nitro-5-(4-pyridinyl)-2(1H)- pyridinone a molar equivalent quantity of the corresponding 3-nitro-5-PY-6-Q-2(1H)-pyridinone, it is contemplated that there can be obtained the 2,3-dichloro-5-PY-6-Q-pyridines of Examples F-2 through FE-17.

F-2. 2,3-Dichloro-6-methyl-5-(4-pyridinyl)pyridine, using 6-methyl-3-nitro-5-(4-pyridinyl)-2(1H)-pyridinone.

F-3. 2,3-Dichloro-6-ethyl-5-(4-pyridinyl)pyridine, using 6-ethyl-3-nitro-5-(4-pyridinyl)-2(1H)-pyridinone.

F-4. 2,3-Dichloro-6-methyl-5-(3-pyridinyl)pyridine, using 6-methyl-3-nitro-5-(3-pyridinyl)-2(1H)pyridinone.

F-5. 2,3-Dichloro-6-n-propyl-5-(4-pyridinyl)pyridine, using 3-nitro-6-N-propyl-5-(4-pyridinyl)-2(1H)-pyridinone.

F-6. 2,3-Dichloro-6-isopropyl-5-(4-pyridinyl)-pyridine, using 3-nitro-6-isopropyl-5-(4-pyridinyl)-2(1H)-pyridinone.

F-7. 2,3-Dichloro-6-n-butyl-5-(4-pyridinyl)pyridine, using 6-n-butyl-3-nitro-5-(4-pyridinyl)-2(1H)-pyridinone.

F-8. 2,3-Dichloro-6-isobutyl-5-(4-pyridinyl)pyridine using 6-isobutyl-3-nitro-5-(4-pyridinyl)-2(1H)-pyridinone.

F-9. 2,3-Dichloro-5-(4-pyridinyl)-6-tert.-butylpyridine, using 3-nitro-5-(4-pyridinyl)-6-tert.-butyl-2(1H)-pyridinone.

F-10. 2,3-Dichloro-6-n-pentyl-5-(4-pyridinyl)pyridine, using 3-nitro-6-n-pentyl-5-(4-pyridinyl)-2(1H)-pyridinone.

F-11. 2,3-Dichloro-6-ethyl-5-(2-methyl-4-pyridinyl)-pyridine, using 6-ethyl-3-nitro-5-(2-methyl-4-pyridinyl)-2(1H)-pyridinone.

F-12. 2,3-Dichloro-6-ethyl-5-(3-pyridinyl)pyridine, using 6-ethyl-3-nitro-5-(3-pyridinyl)-2(1H)-pyridinone.

F-13. 2,3-Dichloro-6-methyl-5-(2,6-dimethyl-4-pyridinyl)pyridine, using 6-methyl-5-(2,6-dimethyl-4-pyridinyl)-3-nitro-2(1H)-pyridinone.

F-14. 2,3-Dichloro-5-(2-methyl-3-pyridinyl)pyridine, using 3-nitro-5-(2-methyl-3-pyridinyl)-2(1H)-pyridinone.

F-15. 2,3-Dichloro-5-(5-methyl-3-pyridinyl)pyridine, using 3-nitro-5-(5-methyl-3-pyridinyl)-2(1H)-pyridinone.

F-16. 2,3-Dichloro-5-(3-ethyl-4-pyridinyl)pyridine, using 3-nitro-5-(3-ethyl-4-pyridinyl)-2(1H)-pyridinone.

F-17. 2,3-Dichloro-5-(4-pyridinyl)pyridine also can be prepared following the procedure described in Example F-1 but using in place of phenylphosphonic dichloride a molar equivalent quantity of phosphorus oxychloride in an autoclave. Similarly, by using phosphorus oxybromide in place of phosphorus oxychloride, there can be obtained 2,3-dibromo-5-(4-pyridinyl)pyridine.

F-18. 3-Bromo-2-chloro-5-(4-pyridinyl)pyridine—A mixture containing 64 g. of 3-bromo-5-(4-pyridinyl)-2(1H)-pyridinone, 400 ml. of phosphorus oxychloride and 10 ml. was refluxed for thirty minutes and allowed to stand overnight at room temperature. The excess $POCl_3$ and solvent were distilled off in vacuo; the residue was dissolved in water and neutralized with 35% aqueous sodium hydroxide solution. The separated product was collected, washed with water, dried and recrystallized from ethanol to yield 39 g. of 3-bromo-2-chloro-5-(4-pyridinyl)pyridine, m.p. 150°-155° C. Another 9 g. of product was obtained by concentrating the ethanolic mother liquor.

Following the procedure described in Example F-18 but using in place of 3-bromo-5-(4-pyridinyl)-2(1H)-pyridinone a molar equivalent quantity of the corresponding 3-halo-5-PY-6-Q-2(1H)-pyridinone, it is contemplated that there can be obtained the 2,3-dihalo-5-PY-6-Q-2(1H)-pyridinones of Examples F-19 through F-30.

F-19. 3-Bromo-2-chloro-6-methyl-5-(4-pyridinyl)-pyridine.

F-20. 2,3-Dichloro-6-methyl-5-(4-pyridinyl)-pyridine.

F-21. 2,3-Dichloro-6-ethyl-5-(4-pyridinyl)pyridine.

F-22. 2,3-Dichloro-6-methyl-5-(3-pyridinyl)-pyridine.

F-23. 2,3-Dichloro-6-n-propyl-5-(4-pyridinyl)-pyridine.

F-24. 3-Bromo-2-chloro-6-isopropyl-5-(4-pyridinyl)-pyridine.

F-25. 3-Bromo-2-chloro-6-n-butyl-5-(4-pyridinyl)-pyridine.

F-26. 2,3-Dichloro-6-isobutyl-5-(4-pyridinyl)-pyridine.

F-27. 3-Bromo-2-chloro-5-(4-pyridinyl)-6-tert.-butyl-pyridine.

F-28. 2,3-Dichloro-6-n-pentyl-5-(4-pyridinyl)-pyridine.

F-29. 3-Bromo-2-chloro-6-ethyl-5-(2-methyl-4-pyridinyl)-pyridine.

F-30. 2,3-Dichloro-6-ethyl-5-(3-pyridinyl)pyridine.

G. 2-[$R_1$NHN(R)]-3-Q'-5-PY-6-Q-pyridines

G-1. 3-Chloro-5-(4-pyridinyl)pyridine-2-hydrazine, alternatively named 5-chloro-6-hydrazino-[3,4'-bipyridine]-A mixture containing 9 g. of 2,3-dichloro-5-(4-pyridinyl)pyridine, 50 ml. of 100% hydrazine hydrate and 50 ml. of ethanol was refluxed for one hour and then cooled. The separated hydrazine hydrochloride was filtered off and the filtrate was heated in vacuo to remove the solvent to yield 7 g. of 3-chloro-5-(4-pyridinyl)-pyridine-2-hydrazine in free base form. Said free base form was recrystallized from dimethylformamide and then dissolved in 6 N hydrogen chloride and the solution treated with isopropyl alcohol. The mixture was cooled and the separated product was collected, washed with ether and dried in vacuo at 70° C. to yield 5 g. of 3-chloro-5-(4-pyridinyl)pyridine-2-hydrazine dihydrochloride, m.p. 298°-300° C. with decomposition.

Other acid-addition salts of 3-chloro-5-(4-pyridinyl)-pyridine-2-hydrazine are conveniently prepared by adding to a mixture of 2 g. of 3-chloro-5-(4-pyridinyl)pyridine-2-hydrazine in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-chloro-5-(4-pyridinyl)-pyridine-2-hydrazine and the appropriate acid, e.g., lactic or hydrochloric acid, to prepare respectively the monolactate or monohydrochloride salt in aqueous solution.

G-2. 5-(4-Pyridinyl)pyridine-2-hydrazine, alternatively named 6-hydrazino-[3,4'-bipyridine]—A mixture containing 21.6 g. of 2-chloro-5-(4-pyridinyl)pyridine, 110 ml. of 97% hydrazine hydrate and 200 ml. of isopropyl alcohol was refluxed with stirring for about eight hours and then concentrated to a volume of about 100 ml. and allowed to cool. The precipitated yellow solid was collected, recrystallized from acetonitrile dried at 70° C. in a vacuum oven at 100 mm. over $P_2O_5$ to yield 10 g. of 5-(4-pyridinyl)pyridine-2-hydrazine, m.p. 165°–168° C.

Acid-addition salts of 5-(4-pyridinyl)pyridine-2-hydrazine are conveniently prepared by adding to a mixture of 2 g. of 5-(4-pyridinyl)pyridine-2-hydrazine in about 40 ml. of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., dihydrochloride, dimethanesulfonate, sulfate, phosphate, respectively. Also, the acid-addition salt is conveniently prepared in aqueous solution by adding to water with stirring molar equivalent quantities each of 5-(4-pyridinyl)pyridine-2-hydrazine and the appropriate acid, e.g., lactic acid or hydrochloric acid, to prepare respectively the monolactate or monohydrochloride salt in aqueous solution.

Following the procedure described in Example G-2 but using in place of 2-chloro-5-(4-pyridinyl)pyridine a molar equivalent quantity of the appropriate 2-halo-5-PY-6-Q-pyridine and either hydrazine or in place of hydrazine a molar equivalent quantity of the appropriate substituted hydrazine of the formula $RNHNHR_1$, it is contemplated that there can be obtained the 2-[$R_1$NH(R)]-5-PY-6-Q-pyridines of Examples G-3 through G-19.

G-3. 5-(4-Pyridinyl)pyridine-2-hydrazine, using 2-bromo-5-(4-pyridinyl)pyridine and hydrazine.

G-4. 5-(3-Pyridinyl)pyridine-2-hydrazine, using 2-chloro-5-(3-pyridinyl)pyridine and hydrazine.

G-5. $N_1$-Methyl-$N_1$-[5-(2-methyl-3-pyridinyl)-2-pyridinyl]hydrazine, using 2-chloro-5-(2-methyl-3-pyridinyl)pyridine and N-methylhydrazine.

G-6. $N_1,N_2$-Dimethyl-$N_1$-[5-(5-methyl-3-pyridinyl)-2-pyridinyl]hydrazine, using 2-chloro-5-(5-methyl-3-pyridinyl)pyridine and $N_1,N_2$-dimethylhydrazine.

G-7. $N_1$-Ethyl-$N_1$-[5-(3-ethyl-4-pyridinyl)-2-pyridinyl]hydrazine, using 2-chloro-5-(3-ethyl-4-pyridinyl)pyridine and N-ethylhydrazine.

G-8. 6-Methyl-5-(4-pyridinyl)pyridine-2-hydrazine, using 2-chloro-6-methyl-5-(4-pyridinyl)pyridine and hydrazine.

G-9. $N_1$-(2-Hydroxyethyl)-$N_1$-[6-ethyl-5-(4-pyridinyl)-2-pyridinyl]hydrazine, using 2-chloro-6-ethyl-5-(4-pyridinyl)pyridine and N-(2-hydroxyethyl)-hydrazine.

G-10. $N_1$-(n-Propyl)-$N_1$-[6-methyl-5-(3-pyridinyl)-2-pyridinyl]hydrazine, using 2-chloro-6-methyl-5-(3-pyridinyl)pyridine and N-(n-propyl)hydrazine.

G-11. $N_1$-Isobutyl-$N_1$-[6-n-propyl-5-(4-pyridinyl)-2-pyridinyl]hydrazine, using 2-chloro-6-n-propyl-5-(4-pyridinyl)pyridine and N-isobutylhydrazine.

G-12. 6-Isopropyl-5-(4-pyridinyl)pyridine-2-hydrazine, using 2-chloro-6-isopropyl-5-(4-pyridinyl)pyridine and hydrazine.

G-13. $N_1$-Methyl-$N_1$-[6-n-butyl-5-(4-pyridinyl)-2-pyridinyl]hydrazine, using 6-n-butyl-2-chloro-5-(4-pyridinyl)pyridine and methylhydrazine.

G-14. 6-Isobutyl-5-(4-pyridinyl)pyridine-2-hydrazine, using 2-chloro-6-isobutyl-5-(4-pyridinyl)pyridine and hydrazine.

G-15. 5-(4-Pyridinyl)-6-tert.-butylpyridine-2-hydrazine using 2-chloro-5-(4-pyridinyl)-6-tert.-butylpyridine and hydrazine.

G-16. 6-n-Pentyl-5-(4-pyridinyl)pyridine-2-hydrazine using 2-chloro-6-n-pentyl-5-(4-pyridinyl)pyridine and hydrazine.

G-17. $N_1,N_2$-Diethyl-$N_1$-[6-ethyl-5-(2-methyl-4-pyridinyl)-2-pyridinyl]hydrazine, using 2-chloro-6-ethyl-5-(2-methyl-4-pyridinyl)pyridine and $N_1,N_2$-diethylhydrazine.

G-18. $N_1,N_2$-bis(2-Hydroxyethyl)-$N_1$-[6-ethyl-5-(3-pyridinyl)-2-pyridinyl]hydrazine, using 2-chloro-6-ethyl-5-(3-pyridinyl)pyridine and $N_1,N_2$-bis(2-hydroxyethyl)hydrazine.

G-19. $N_1$-(n-Hexyl)-$N_1$-[6-methyl-5-(2,6-dimethyl-4-pyridinyl)-2-pyridinyl]hydrazine, using 2-chloro-6-methyl-5-(2,6-dimethyl-4-pyridinyl)pyridine and N-(n-hexyl)hydrazine.

Following the procedure described in Example G-1 but using in place of 2,3-dichloro-5-(4-pyridinyl)pyridine a molar equivalent quantity of the appropriate 2,3-dihalo-5-PY-6-Q-pyridine and either hydrazine or in place of hydrazine a molar equivalent quantity of the appropriate substituted hydrazine of the formula $RNHNHR_1$, it is contemplated that there can be obtained the 2-[$R_1$NH(R)]-3-halo-5-PY-6-Q-pyridines of Examples G-20 through G-36.

G-20. 3-Chloro-6-methyl-5-(4-pyridinyl)pyridine-2-hydrazine, using 2,3-dichloro-6-methyl-5-(4-pyridinyl)pyridine and hydrazine.

G-21. 3-Chloro-6-ethyl-5-(4-pyridinyl)pyridine-2-hydrazine, using 2,3-dichloro-6-ethyl-5-(4-pyridinyl)pyridine and hydrazine.

G-22. $N_1$-[3-Chloro-6-methyl-5-(3-pyridinyl)-2-pyridinyl]-$N_1$-methylhydrazine, using 2,3-dichloro-6-methyl-5-(3-pyridinyl)pyridine and N-methylhydrazine.

G-23. $N_1$-[3-Chloro-6-n-propyl-5-(4-pyridinyl)-2-pyridinyl]-$N_1,N_2$-dimethylhydrazine, using 2,3-dichloro-6-n-propyl-5-(4-pyridinyl)pyridine and $N_1,N_2$-dimethylhydrazine.

G-24. $N_1$-[3-Chloro-6-isopropyl-5-(4-pyridinyl)-2-pyridinyl]-$N_1$-ethylhydrazine, using 2,3-dichloro-6-isopropyl-5-(4-pyridinyl)pyridine and N-ethylhydrazine.

G-25. 6-n-Butyl-3-chloro-5-(4-pyridinyl)-2-pyridinehydrazine, using 6-n-butyl-2,3-dichloro-5-(4-pyridinyl)pyridine and hydrazine.

G-26. $N_1$-[3-Chloro-6-isobutyl-5-(4-pyridinyl)-2-pyridinyl]-$N_1$-(n-propyl)hydrazine, using 2,3-dichloro-6-isobutyl-5-(4-pyridinyl)pyridine and N-(n-propyl)hydrazine.

G-27. $N_1$-[3-Chloro-6-tert.-butyl-5-(4-pyridinyl)-2-pyridinyl]-$N_1$-methylhydrazine, using 2,3-dichloro-6- tert.-butyl-5-(4-pyridinyl)pyridine and N-methylhydrazine.

G-28. 3-Chloro-6-n-pentyl-5-(4-pyridinyl)pyridine-2-hydrazine, using 2,3-dichloro-6-n-pentyl-5-(4-pyridinyl)pyridine and hydrazine.

G-29. $N_1$-[3-Chloro-6-ethyl-5-(2-methyl-4-pyridinyl)-2-pyridinyl]-$N_1$-(2-hydroxyethyl)hydrazine, using 2,3-dichloro-6-ethyl-5-(2-methyl-4-pyridinyl)pyridine and N-(2-hydroxyethyl)hydrazine.

G-30. $N_1$-[3-Chloro-6-ethyl-5-(3-pyridinyl)-2-pyridinyl]-$N_1,N_2$-diethylhydrazine, using 2,3-dichloro-6-ethyl-5-(3-pyridinyl)pyridine and $N_1,N_2$-diethylhydrazine.

G-31. $N_1$-[3-Chloro-6-methyl-5-(2,6-dimethyl-4-pyridinyl)-2-pyridinyl]-$N_1$-ethylhydrazine, using 2,3-dichloro-6-methyl-5-(2,6-dimethyl-4-pyridinyl)pyridine and N-ethylhydrazine.

G-32. $N_1$-[3-Chloro-5-(2-methyl-3-pyridinyl)-2-pyridinyl]-$N_1,N_2$-dimethylhydrazine, using 2,3-dichloro-5-(2-methyl-4-pyridinyl)pyridine and $N_1,N_2$-dimethylhydrazine.

G-33. $N_1$-[3-Chloro-5-(5-methyl-3-pyridinyl)-2-pyridinyl]-$N_1,N_2$-bis(2-hydroxyethyl)hydrazine, using 2,3-dichloro-5-(5-methyl-3-pyridinyl)pyridine and $N_1,N_2$-bis(2-hydroxyethyl)hydrazine.

G-34. $N_1$-[3-Chloro-5-(3-ethyl-4-pyridinyl)-2-pyridinyl]-$N_1$-methylhydrazine, using 2,3-dichloro-5-(3-ethyl-4-pyridinyl)pyridine and N-methylhydrazine.

G-35. 3-Bromo-5-(4-pyridinyl)pyridine-2-hydrazine, using 2,3-dibromo-5-(4-pyridinyl)pyridine or 3-bromo-2-chloro-5-(4-pyridinyl)pyridine and hydrazine.

G-36. 3-Bromo-6-ethyl-5-(2-methyl-4-pyridinyl)pyridine-2-hydrazine, using 3-bromo-2-chloro-5-(2-methyl-4-pyridinyl)pyridine and hydrazine.

The usefulness of the compounds of formula I or salt thereof as cardiotonic agents is demonstrated by their effectiveness in standard pharmacological test procedures, for example, in causing a significant increase in contractile force in the Isolated Cat Atria and Papillary Muscle Procedure and in causing a significant increase in cardiac contractile force in the Anesthetized Dog Procedure with low or minimal changes in heart rate and blood pressure. Detailed descriptions of these test procedures appear in U.S. Pat. No. 4,072,746, issued Feb. 7, 1980.

When tested by the above-noted Isolated Cat Atria and Papillary Muscle Procedure, the compounds of formula I or salt thereof when tested at doses of 10, 30 and/or 100 µg./ml., were found to cause a significant increase, that is, greater than 25%, in papillary muscle force and a significant increase, that is, greater than 25%, in right atrial force, while causing only a low percentage increase (about one-half or less than the percentage increase in right atrial force or papillary muscle force) in right atrial rate. For example, when tested at 30 and 100 µg./ml. by said procedure, the compound of Example G-1 was found to cause respective increases of 25% and 47% in papillary muscle force; when tested at 10, 30 and 100 µg./ml. by said procedure the compound of Example G-2 was found to cause respective increases of 34%, 81% and 236% in papillary muscle force and to cause respective increases of 19%, 62% and 125% in right atrial force at said doses.

The present invention includes within its scope a cardiotonic composition for increasing cardiac contractility, said composition comprising a pharmaceutically-acceptable carrier and, as the active component thereof, a cardiotonically-effective amount of a 2-[$R_1$NHN(R)]-3-Q'-5-PY-6-Q-pyridine of formula I or pharmaceutically-acceptable acid-addition salt thereof. The invention also includes within its scope the method for increasing cardiac contractility in a patient requiring such treatment which comprises administering orally or parenterally in a solid or liquid dosage form to such patient a cardiotonically-effective amount of said pyridine of formula I or pharmaceutically-acceptable acid-addition or cationic salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose and lactose. These compositions can also contain additional substances other than inert diluents, e.g., lubricating agents, such as magnesium stearate, talc and the like.

Liquid compositions for oral administration include pharmaceutically-acceptable emulsions, solution, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active components in said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 2-[$R_1$NHN(R)]-3-Q'-5-PY-6-Q-pyridine having the formula

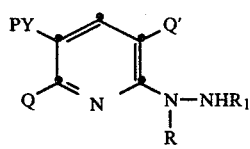

wherein Q is hydrogen or lower-alkyl, PY is 4- or 3-pyridinyl or 4- or 3-pyridinyl having one or two lower-alkyl substituents, Q' is hydrogen or halo, R is hydrogen, lower-alkyl or lower-hydroxyalkyl, and $R_1$ is hydrogen, or when R is other than hydrogen $R_1$ is the same as R, or pharmaceutically-acceptable acid-addition or cationic salt thereof.

2. A compound according to claim 1 where PY is 4-pyridinyl or 3-pyridinyl.

3. A compound according to claim 1 where Q is hydrogen, methyl or ethyl and Q' is hydrogen or chloro.

4. A compound according to claim 1 where R is hydrogen, methyl, ethyl or 2-hydroxyethyl.

5. 3-Chloro-5-(4-pyridinyl)pyridine-2-hydrazine or pharmaceutically-acceptable acid-addition salt thereof.

6. 5-(4-Pyridinyl)pyridine-2-hydrazine or pharmaceutically-acceptable acid-addition salt thereof.

7. A cardiotonic composition for increasing cardiac contractility, said composition comprising a pharmaceutically-acceptable inert carrier and, as the active component thereof, a cardiotonically-effective amount of a 2-[$R_1$NHN(R)]-3-Q'-5-PY-6-Q-pyridine or pharmaceutically-acceptable acid-addition salt thereof, where Q is hydrogen or lower-alkyl, PY is 4- or 3-pyridinyl or 4- or 3-pyridinyl having one or two lower-alkyl substituents, Q' is hydrogen or halo, R is hydrogen, lower-alkyl or lower-hydroxyalkyl, and $R_1$ is hydrogen or when R is other than hydrogen $R_1$ is the same as R.

8. A composition according to claim 7 where Q is hydrogen, methyl or ethyl, Py is 4-pyridinyl or 3-pyridinyl, Q' is chloro or hydrogen, R is hydrogen, methyl, ethyl or 2-hydroxyethyl, and $R_1$ is either hydrogen or the same as R.

9. A composition according to claim 8 where the active component is 5-(4-pyridinyl)pyridine-2-hydrazine or pharmaceutically-acceptable acid-addition salt thereof.

10. The method for increasing cardiac contractility in a patient requiring such treatment which comprises administering orally or parenterally in a solid or liquid dosage form to such a patient a cardiotonically-effective amount of 2-[$R_1$NHN(R)]-3-Q'-5-PY-6-Q-pyridine or pharmaceutically-acceptable acid-addition salt thereof, where Q is hydrogen or lower-alkyl, PY is 4- or 3-pyridinyl or 4- or 3-pyridinyl having one or two lower-alkyl substituents, Q' is hydrogen or halo, R is hydrogen, lower-alkyl or lower-hydroxyalkyl, and $R_1$ is hydrogen or when R is other than hydrogen $R_1$ is the same as R.

11. The method according to claim 10 where Q is hydrogen, methyl or ethyl, PY is pyridinyl or 3-pyridinyl, Q' is chloro or hydrogen, R is hydrogen, methyl, ethyl or 2-hydroxyethyl, and $R_1$ is either hydrogen or the same as R.

12. The method according to claim 11 where the active component is 5-(4-pyridinyl)pyridine-2-hydrazine or pharmaceutically-acceptable acid-addition salt thereof.

13. The process which comprises reacting 2-halo-3-Q'-5-PY-6-Q-pyridine with $R_1$NHNHR to produce 2-[$R_1$NHN(R)]-3-Q'-5-PY-6-Q-pyridine according to claim 1 where 2-halo is bromo or chloro, and Q', PY, Q, $R_1$ and R have the meanings given in claim 1.

14. The process according to claim 13 where 2-halo is 2-chloro, Q is hydrogen, methyl or ethyl, PY is 4-pyridinyl or 3-pyridinyl, Q' is chloro or hydrogen, R is hydrogen, methyl, ethyl or 2-hydroxyethyl, and $R_1$ is either hydrogen or the same as R.

* * * * *

UNITED STATES PATENT AND TRADEMARK OFFICE
CERTIFICATE OF CORRECTION

PATENT NO. : 4,331,672
DATED : May 25, 1982
INVENTOR(S) : George Y. Lesher et al.

It is certified that error appears in the above-identified patent and that said Letters Patent are hereby corrected as shown below:

Abstract, line 1, "5-Py-6" should read -- 5-PY-6 --.

Column 6, line 29, "2(1H)-pyridine" should read -- 2(1H)-pyridinone --.

Signed and Sealed this

First Day of February 1983

[SEAL]

Attest:

GERALD J. MOSSINGHOFF

Attesting Officer

Commissioner of Patents and Trademarks